United States Patent [19]

Malmqvist-Granlund et al.

[11] Patent Number: 5,178,868
[45] Date of Patent: Jan. 12, 1993

[54] DOSAGE FORM

[75] Inventors: Karin Malmqvist-Granlund, Florvägen; Christer Hermansson, Spårsnögatan; Sören Kulstad, Husarvägen, all of Sweden

[73] Assignee: Kabi Pharmacia Aktiebolaq, Helsingborg, Sweden

[21] Appl. No.: 770,767

[22] Filed: Oct. 4, 1991

Related U.S. Application Data

[63] Continuation of Ser. No. 426,747, Oct. 24, 1989, abandoned.

Foreign Application Priority Data

Oct. 26, 1988 [SE] Sweden .................. 8803822

[51] Int. Cl.$^5$ .................. A61K 9/58; A61K 9/16
[52] U.S. Cl. .................. 424/490; 424/78.18; 424/462; 424/473; 424/482; 424/497
[58] Field of Search .............. 424/462, 490, 496, 497, 424/78, 473, 482

[56] References Cited

U.S. PATENT DOCUMENTS

| 3,538,214 | 11/1970 | Polii et al. | 424/19 |
|---|---|---|---|
| 4,256,108 | 3/1981 | Theeuwes | 128/260 |
| 4,557,925 | 12/1985 | Lindahl et al. | 424/19 |
| 4,606,909 | 8/1986 | Bechgaard et al. | 424/21 |
| 4,687,660 | 8/1987 | Baker et al. | 424/465 |
| 4,728,513 | 3/1988 | Ventouras | 424/461 |
| 4,824,678 | 4/1989 | Lindahl | 424/473 |

FOREIGN PATENT DOCUMENTS

| 0153104 | 8/1985 | European Pat. Off. |
| 0171457 | 2/1986 | European Pat. Off. |
| 0202051 | 11/1986 | European Pat. Off. |
| 435897 | 10/1984 | Sweden |
| 1186990 | 4/1970 | United Kingdom |
| 1468172 | 3/1977 | United Kingdom |

*Primary Examiner*—Thurman K. Page
*Assistant Examiner*—G. S. Kishore
*Attorney, Agent, or Firm*—Pravel, Gambrell, Hewitt, Kimball & Krieger

[57] ABSTRACT

The invention relates to an oral pharmaceutical multiple units formulation made up of individual cores containing a pharmacologically active substance, the cores being provided with a coating consisting essentially of a polymer that is insoluble in, impermeable to and non-soluble in water and in gastrointestinal fluids, and a water-soluble pore-creating substance, which is randomly distributed in said polymer, whereby said coated cores form units providing an essential zero order diffusion controlled release rate of said active substance. The invention also comprises a method of preparing these formulations.

8 Claims, No Drawings

DOSAGE FORM

This is a continuation of co-pending application Ser. No. 426,747 filed on Oct. 24, 1989, now abandoned.

The present invention relates to an oral pharmaceutical controlled release multiple units dosage form in which individual units containing an active substance are surrounded by a coating which releases the active substance through diffusion.

TECHNICAL BACKGROUND

The term "controlled release multiple units formulation" (Bechgaard Hegermann Nielsen, 1978) indicates a pharmaceutical formulation comprising a multiplicity (typically at least 100) of individual coated (or "microencapsulated") units contained in the formulation in such a form that the individual units will be made available from the formulation upon disintegration of the formulation in the stomach of animals, including humans, who have ingested the formulation. Typically, the multiple units formulation may be a gelatin capsule or a tablet which disintegrates in the stomach to make available a multiplicity of coated units.

Controlled release multiple units formulations aim at a controlled release of active substance in a predetermined pattern to reduce and delay the peak plasma concentration without affecting the extent of drug availability. Due to a lower peak plasma concentration, the frequency of undesirable side-effects may be reduced, and due to the delay in the time it takes to obtain the peak plasma concentration and the prolongation of the time above the therapeutically active plasma concentration, the dosage frequency may be reduced to a dosage taken only twice or once a day, in order to improve patient compliance.

A further advantage of the controlled release multiple units dosage form is that high local concentration of the active substance in the gastrointestinal system is avoided, due to the units being distributed freely throughout the gastrointestinal tract.

Drug release from a controlled release dosage form is generally controlled by a coating outside an active core. The release can be achieved a) by diffusion: the coating swells in aqueous environment so that the active substance can diffuse through the stagnant liquid phase contained in the coating polymer; or b) by osmosis: the coating is semipermeable, i.e. only water can penetrate the coating polymer and dissolve the active substance, this will lead to a pressure buildup inside the coating, in order to allow the active to be released from the unit a hole or channel with a well defined area must be formed in the coating, this can be achieved either by laser drilling (SE patent 435 897—U.S. Pat. No. 4,256,108 to Alza) or by incorporation of a substance which will form the channels by erosion after ingestion (U.S. Pat. No. 4,687,660 and European patent application 0 171 457 to Wellcome), should the coating have any weak spots or cracks in it these will increase the release area and as a result give varying dissolution rates for different units, i.e. zero order release will not be achieved for the hole dose, or c) by erosion: the coating will disintegrate by a process dependent on, e.g. enzymes or pH and leave the active core exposed to rapid dissolution. The importance of a pH independent diffusion with respect to obtaining a reproducible rate of availability and to minimizing intra- and intersubject variations is known (GB patent 1,468,172 and Bechgaard & Baggesen, 1980). It is also known that controlled drug release in vivo can be achieved through an erodable process by enteric coating of a multiple units dosage form (Green, 1966; McDonald et al., 1977; Bogentoft et al., 1978).

The present invention deals with multiple units dosage forms controlled by diffusion membranes. Contrary to previously known diffusion membranes used for multiple unit dosages the membrane according to the invention is non-swellable in water and gastrointestinal fluids. Furthermore, the polymer used must be insoluble in and impermeable to water and pores are formed in the membrane after ingestion by a pH independent erosion process. The pores will give the coating a sponge-like appearance and will be filled with stagnant liquid where the active substance can diffuse out from the core.

DISCLOSURE OF THE INVENTION

A number of coatings employed in connection with pharmaceutical controlled release multiple units formulations have been observed to suffer from the disadvantage that they change their release characteristics in the course of time. This means that it is not possible to maintain a reproducible release rate of an active substance contained in the multiple units formulation as a variable release rate has been observed for such coatings. In accordance with the present invention, it has unexpectedly been found that by selecting a special type of controlled release system which has not previously been used or disclosed for multiple units formulations many problems connected to multiple units formulations can be avoided.

In macro scale, i.e. for tablets, controlled release systems based on coatings containing pore-creating substances have been disclosed in, e.g. the GB patent 1,186,990, the U.S. patent 3,538,214 and in the U.S. Pat. No. 4,557,925. The present release system is based on the principle of coating a core including pharmacological active substance with a film essentially consisting of polymer that is insoluble in and impermeable to water and gastrointestinal fluids, and in which a water soluable pore-creating substance is randomly distributed. It is also required that the polymer is non-swellable in water and gastrointestinal fluids. When applying this controlled release system to multiple units formulations it was unexpectedly found that important advantages could be obtained.

It was thus found that it is possible to coat different types of particles, including crystals, in ordinary coating equipment, i.e. in different types of standard equipment normally available in a pharmaceutical industry. From this follows that the manufacturing process is comparatively easy and cheap. Additionally, it was found that a uniform essentially zero order controlled release rate could be obtained also when relatively non-uniform particles were used as cores.

This is usually not the case in conventional multiple units controlled release formulations. For example diffusion controlled release from multiple units where the polymer swells are dependent on the thickness of the diffusion layer which will differ with time since the polymer will release the active substance while the swelling continues. This will lead to different release rates at the beginning and end of the release period which will result in a release more similar to first order release than zero order. Osmotic controlled multiple units on the other hand are dependent on both the ability of the substances in the core to draw water into it, which may lead to lowered release rate at the end of the release period if the osmotic active and drug active substances are not the same, and the coating quality, which, if it has any weak spots or cracks in it, increases the release area. Such defects give varying dissolution rates for different units, i.e. zero order release will not be achieved for the multiplicity of the units contained in a dose.

Another advantage of the present invention is the possibility of adjusting the release rate by changing the film thickness. In currently commercially used multiple unit systems this possibility seems to exist in a rather unpredictable manner and only up to a certain film thickness. In the present system, on the contrary, an essentially linear correlation exists between the release rate and the film thickness. This means that for a given type of film, the release rate decreases when the film thickness increases in a proportional manner in accordance with Fick's first law of diffusion.

It is also possible to change the release rate by changing the ratio between the pore-creating substance and the coating polymer. This gives the present system a unique possibility to utilize active substances with very different solubilities, which is a great advantage over the existing multiple units controlled release systems.

Thus, one aspect of the invention relates to an oral pharmaceutical controlled release multiple units formulation characterized by individual units containing an active substance, which units are provided with an outer coating consisting essentially of a polymer that is insoluble in, impermeable to and non-swellable in water and gastrointestinal fluids, and a water soluble pore-creating substance which is randomly distributed in the polymer. Another aspect of the invention is a formulation in which units of the type described above are combined with uncoated units which comprise the same or another active substance for instant release thereof, and/or with non-diffusion coated units which have been provided with a coating selected from hydrophilic coatings, hydrophobic coatings, water-based coatings and organic coatings imparting desired properties to the unit such as acid or alkali resistance, storage stability, taste masking, light stability, coloring, improved processability, etc. The ratio between diffusion coated and uncoated or non-diffusion coated units in the composition may be adjusted according to, for instance, the desired release characteristics of the composition, but is preferably in the range of about 10:90 to 90:10 of diffusion coated units to uncoated or non-diffusion coated units.

The oral pharmaceutical controlled release multiple units formulation according to the invention will typically be a gelatin capsule containing a multiplicity of the units, typically more than 100, a sachet containing a multiplicity of the units, typically more than 500, or a tablet made from a multiplicity of the units, typically more than 100, in such a manner that the tablet will after ingestion disintegrate in the stomach into a multiplicity of individual units. In each of the three above mentioned formulations, the units will be freely distributed throughout the gastrointestinal tract shortly after ingestion.

DETAILED DESCRIPTION OF THE INVENTION

Coating

The coating polymer should have good film-forming and adhesive properties, and should be readily soluble in organic solvents such as acetone, methylene chloride, methylethyl ketone or mixtures of acetone and ethanol or methylene chloride. Furthermore, the polymer used must be insoluble in and impermeable to water. Suitable polymers are non-swelling celluose derivatives, acrylic polymers and vinyl polymers. Preferably the coating polymer is a polymer containing 80-95% weight by weight vinyl chloride, 1-19% weight by weight vinyl acetate and 0-10% weight by weight vinyl alcohol, preferably containing 88-94% weight by weight vinyl chloride, 2-5% weight by weight vinyl acetate and 3-5% weight by weight vinyl alcohol.

Preferably plasticizers also are present in the coating. The amount may vary between 1 to 50% weight by weight of the coating polymer, preferably between 10 and 40%. Examples of suitable plasticizers are acetyltributylcitrate, polyethylene glycol, blown castor oil and glyceryl triacetate. Furthermore, the coating may include sodium bicarbonate as stabilizing agent in amounts between 1 and 20% weight by weight of the coating polymer, preferably 5 to 15% weight by weight of the coating polymer.

The pore-creating substance used according to the present invention should be highly water-soluble, insoluble in the solvent used for coating, pharmacologically acceptable and essentially free from own pharmacological effects in the amounts used. Especially preferred are sugars such as saccharose and lactos, and salts such as sodium chloride.

The particle size of the pore-creating substance may vary between 0.1 and 100, preferably between 0.5 and 50 $\mu$m. The ratio between the amount of pore-creating substance and coating polymer depends on the desired dissolution rate. Generally the ratio should be between 0.05 and 5, preferably between 0.1 and 2.

The coating thickness is also dependent on the desired dissolution rate. It may vary between 5 and 300 $\mu$m, preferably 10 and 150 $\mu$m.

Cores

The individual units of the multiple units formations according to the invention are individual cores, at least some of said cores being provided a coating, consist of crystals or pellets. The crystal units are substantially monolitic crystals. The pellets are constituted by a combination of active substance and excipients. One major type of pellets consists of an excipient seed-particle with active substance applied to its surface. Typically pellets of this type are the so-called "non-pareil" pellets where the seeds are in the form of spherical particles of saccharose. In another pellet formulation principle of this type the seeds are in the form of crystalline saccharose.

Another major type of pellets consists of cross-sectionally substantially homogenous particles prepared, e.g. wet-granulation or extrusion.

The diameter of the cores is normally about 0.1-1.5 mm, preferably about 0.4-1.2 mm, preferably with a range of about 0.4 mm within a specific formulation.

Pharmacological Active Substance

The pharmacological active substance in the formulations according to the invention may be any active substance which is advantageously administered in a controlled release multiple units formulations. Examples of suitable active substances are found among almost all therapeutic groups, including diuretics, antiepileptics, sedatives, antiarrythmics, antirheumatics, β-blockers, vasodilators, analgesics, bronchodilators, hormones, vitamines, oral antidiabetics, antibiotics, antihypertensives, anti-inflammatory drugs, antimicrobial agents and antidepressants, polypetides, enzymes and mucopolysaccharides.

As examples of phramacological active substances may be mentioned phenylpropanolamine, potassium chloride, quinidine salts, lithium carbonate, acetyl cystein, depyridamol, theophylline, choline theophyllinate, dextropropoxyphene, dextromethorphan, salbutamol, terbutaline, digoxin, furosemide, propranolol, ibuprofen, lidocaine, mepyramine, morphine, nitroglycerine, clonidine, disopyramide, verapamil, captopril, prazocin, nifedipine, diltiazem, paracetamol, idomethacin, ticlopedine, oxybutynin and noscapine.

Among these substances, some are characterized as having a pH-independent solubility, others as having a pH-dependent solubility. Pharmacological active substances having a pH-dependent solubility are preferably incorporated in cores in combination with buffering substances such as sodium bicarbonate, citric acid, succinic acid or tartaric acid, in order to obtain a dissolution of pharmacological active substance which is substantially independent of the gastrointestinal pH variations through which the units will pass.

Method

Generally the method of producing the coated multiple unit preparation according to the invention comprises the steps of dissolving the polymer in a solvent, preparing a suspension of the pore-creating substance, mixing the suspension of pore-creating substance and the solvent solution of the polymer to form a coating fluid, prepare multiple unit cores containing a pharmacological active substance in the form of crystals or pellets, applying the coating fluid to the core units, and drying the units in order to evaporate the solvent and provide polymer-coated multiple units having the water-soluable pore-creating substance randomly distributed within the coating.

The solvent for the polymer can be selected from, e.g. acetone, methylene chloride, methylethyl ketone or mixtures of acetone and ethanol or methylene chloride.

The pore-creating particles are micronized either by dry milling or by wet milling to a defined particle size, preferably between 0.5 $\mu$m and 50 $\mu$m. The particles are dispersed in solvents such as those previously mentioned, and mixed with the terpolymer solution.

The coating fluid may, as previously stated, include a plasticizer and sodium bicarbonate.

Coloring matter can also be incorporated in the coating fluid, and insoluble coloring materials are preferred.

The coating fluid, in the form of a suspension, is then applied on drug-containing cores. A special advantageous feature is that the coating process can be performed in ordinary coating equipment, i.e. in different types of standard equipment normally available in a pharmaceutical industry. This is due to the good film-forming and adhesive properties of the coating material, and the easiness of solvent evaporation from the system. Examples of such coating equipments are pan coating in sugar-coating pans or perforated film-coating pans, Würster coating, and other fluid-bed coating procedures. From this follows that the manufacturing process is comparatively easy and cheap.

The following examples further illustrate the invention but should not be construed as limiting to the invention.

EXAMPLE 1

Theophylline is a weak acid (p$K_a$=8.7) which is poorly soluble in water. The cores used in this example contain 60% theophylline on non-parils and have a particle size of 0.8–1.0 mm. These cores (1.0 kg) are coated with a coating suspension of the following composition:

| | |
|---|---:|
| Terpolymer containing 92% vinylchloride, 4% vinylacetate and 4% vinylalcohol weight by weight | 390 g |
| Micronized succrose (particle size 1–10 $\mu$m) | 930 g |
| Acetyl tributyl citrate | 89 g |
| Blown castor oil | 68 g |
| Sodium bicarbonate | 34 g |
| Aceton | ad 10.000 g |

The coating suspension is applied on the cores with an airless spray-coating device in a coating pan. Samples are taken after the application of 1.0, 2.0 and 3.0 kg of the suspension.

Table 1 shows the dissolution rate of a dose corresponding to 90 mg theophylline. The dissolution testing is performed according to the USP XXI basket method (100 rpm). There is a linear correlation between the release rate and the coating thickness, and the release rate is essentially independent of the pH. A uniform zero order release rate is observed during the major part of the release time.

TABLE 1

| Time (Hours) | Released amount of theophylline (%) | | | |
|---|---|---|---|---|
| | 0.1M TRIS buffer pH 7.4 | | | 0.1M HCL |
| | A | B | C | C |
| 1 | 46 | 18 | 10 | 11 |
| 2 | 84 | 39 | 24 | 28 |
| 3 | 98 | 58 | 37 | 44 |
| 4 | 100 | 76 | 49 | 59 |
| 5 | | 90 | 62 | 73 |
| 6 | | 96 | 73 | 86 |
| 7 | | 99 | 83 | 94 |
| 8 | | | 90 | 99 |
| 9 | | | 94 | 100 |
| 10 | | | 96 | 101 |
| 11 | | | 97 | 101 |
| 12 | | | 98 | 102 |

A: 2.5 mg coating material per cm$^2$ of the cores
B: 5.9 mg coating material per cm$^2$ of the cores
C: 9.0 mg coating material per cm$^2$ of the cores

EXAMPLE 2

Choline theophylline is a salt of the theophylline readily soluble in water. The cores used in this example contain 30% choline theophyllinate on sugar crystals and have a particle size of 0.7–1.0 mm. These cores (1.0 kg) are coated with a suspension of the following compositions:

| | |
|---|---:|
| Terpolymer containing 92% vinylchloride, | 295 g |

-continued

| | |
|---|---|
| 4% vinylacetate and 4% vinylalcohol weight by weight | |
| Micronized succrose (particle size 1-10 μm) | 930 g |
| Acetyl tributyl citrate | 30 g |
| Blown castor oil | 23 g |
| Sodium bicarbonate | 34 g |
| Titanium dioxide | 59 g |
| Acetone | ad 10.000 g |

The coating suspension is applied on the cores with an airless spray-coating device in a coating pan. Samples are taken after the application of 2.0, 2.5 and 3.0 kg of the suspension.

Table 2 shows the dissolution rate of a dose corresponding to 90 mg theophylline. The dissolution rate testing is performed according to the USP XXI basket method (100 rpm). The dissolution rate is considerably higher than in Example 1 due to the much higher solubility of the choline salt of the theophylline than of pure theophylline. Despite the higher dissolution rate there is still a linear correlation between the release rate and the coating thickness.

TABLE 2

| Time | Released amount of theophylline (%) 0.2M TRIS buffer pH 7.4 | | |
|---|---|---|---|
| (Hours) | A | B | C |
| 0.33 | 96 | 86 | 76 |
| 0.67 | 100 | 99 | 98 |
| 1.00 | | 100 | 100 |

A: 3.7 mg coating material per cm² of the cores
B: 4.6 mg coating material per cm² of the cores
C: 5.5 mg coating material per cm² of the cores

EXAMPLE 3

Diltiazem hydrochloride is an ammonium salt readily soluble in water. The cores used in this example contain 44% diltiazem hydrochloride or non-pareils and have a particle size of 0.7-1.1 mm. These cores (0.9 kg) are coated with a coating suspension of the following composition.

| | |
|---|---|
| Terpolymer containing 92% vinylchloride, 4% vinylacetate and 4% vinylalcohol weight by weight | 409 g |
| Micronized sucrose (particle size 1-10 μm) | 930 g |
| Acetyl tributyl citrate | 70 g |
| Blown castor oil | 52 g |
| Sodium bicarbonate | 34 g |
| Aceton | ad 10.000 g |

The coating suspension is applied on the cores with an airless spray-coating device in a coating pan. Samples are taken after the application of 1.6, 2.3 and 3.0 kg of the suspension.

Table 3 shows the dissolution rate of a dose corresponding to 120 mg diltiazem hydrochloride. The dissolution testing is performed according to the USP XXI basket method (100 rpm). The solubility of this ammonium salt is similar to that of the salt in Example 2. The dissolution rate is therefore also similar. Also here the linear correlation between the release rate and the coating thickness is obvious.

TABLE 3

| Time | Released amount of theophylline (%) 0.05M Phosphate buffer pH 7.4 | | |
|---|---|---|---|
| (Hours) | A | B | C |
| 0.25 | 48 | 34 | 27 |
| 0.50 | 79 | 67 | 56 |
| 0.75 | 91 | 85 | 80 |
| 1.00 | 96 | 91 | 85 |
| 1.25 | 98 | 94 | 91 |
| 1.50 | 99 | 97 | 94 |
| 1.75 | 100 | 98 | 96 |
| 2.00 | 101 | 99 | 97 |

A: 6.8 mg coating material per cm² of the cores
B: 9.8 mg coating material per cm² of the cores
C: 12.4 mg coating material per cm² of the cores Having described the invention above, various modifications of the techniques, procedures, material and equipment will be apparent to those in the art. It is intended that all such variations within the scope and spirit of the appended claims be embraced thereby.

We claim:

1. Oral pharmaceutical multiple units formulation comprising individual cores containing a pharmacological active substance, at least some of said cores being provided with a coating consisting essentially of:
   a) a polymer containing 80-95% weight by weight vinyl chloride, 1-19% weight by weight vinyl acetate, and 0% to 10% weight by weight vinyl alcohol; and
   b) a pore-creating substance that is soluble in water and is randomly distributed in said polymer;
   c) whereby said coated cores form units providing an essentially zero-order diffusion controlled release rate of said pharmacological active substance.

2. The formulation of claim 1 wherein said terpolymer contains 88-94% weight by weight vinyl chloride, 2-5% weight by weight vinyl acetate and 3-5% weight by weight vinyl alcohol.

3. The formulation of claim 1 wherein said uncoated cores contain a pharmacological active substance for the instant release thereof.

4. Oral pharmaceutical multiple units formulation comprising individual cores containing a pharmacological active substance, at least some of said cores being provided with a coating consisting essentially of:
   a) a terpolymer containing about 92 percent weight by weight vinyl chloride, about 4 percent weight by weight vinyl acetate, and about 4 percent weight by weight vinyl alcohol; and
   b) micronized sucrose;
   c) whereby said coated cores form units providing an essentially zero-order diffusion controlled release rate of said pharmacological active substance.

5. The formulation of claim 4 wherein said pharmacological active substance is theophylline.

6. The formulation of claim 4 wherein said pharmacological active substance is choline theophyllinate.

7. The formulation of claim 4 wherein said pharmacological active substance is dilitiazem.

8. The formulation of claim 4 wherein said pharmacological active substance is naphtazone.

* * * * *